US011559419B2

(12) United States Patent
Maloney (10) Patent No.: US 11,559,419 B2
(45) Date of Patent: Jan. 24, 2023

(54) FUNCTIONAL ANKLE SUPPORTS WITH IMPROVED MOVEMENT AND COMFORT

(71) Applicant: POD GLOBAL IP PTY LTD, Torquay (AU)

(72) Inventor: Geoffrey Paul Maloney, Torquay (AU)

(73) Assignee: POD GLOBAL IP PTY LTD, Torquay (AU)

( * ) Notice: Subject to any disclaimer, the term of this patent is extended or adjusted under 35 U.S.C. 154(b) by 364 days.

(21) Appl. No.: 15/328,597

(22) PCT Filed: Jul. 27, 2015

(86) PCT No.: PCT/AU2015/000441
§ 371 (c)(1),
(2) Date: Jan. 24, 2017

(87) PCT Pub. No.: WO2016/011493
PCT Pub. Date: Jan. 28, 2016

(65) Prior Publication Data
US 2017/0216073 A1     Aug. 3, 2017

Related U.S. Application Data

(60) Provisional application No. 62/028,866, filed on Jul. 25, 2014.

(51) Int. Cl.
*A61F 5/00* (2006.01)
*A61F 5/01* (2006.01)

(52) U.S. Cl.
CPC ................................. *A61F 5/0111* (2013.01)

(58) Field of Classification Search
CPC .. A61F 5/00; A61F 5/01; A61F 5/0111; A61F 5/0127; A61F 5/012; A61F 5/42; A61F 5/048; A61F 5/0102; A61F 5/052; A61F 5/058; A61F 5/37; A61F 13/00; A61F 5/0113; A61F 5/0123; A61F 5/0104; A61F 5/0195; A61F 5/0585; A61F 2005/0174; A61F 2005/001; A61F 2005/0197; A61F 13/06; A61F 13/064; A61F 13/066;
(Continued)

(56) References Cited

U.S. PATENT DOCUMENTS 3,504,668 A * 4/1970 Boudon ................. A61F 5/0113
602/28
5,219,324 A * 6/1993 Hall ....................... A61F 5/0111
602/27
(Continued)

FOREIGN PATENT DOCUMENTS

DE    102012011466 A1   12/2013
WO   WO 1994/005236 A1   3/1994
WO   WO 2004/043289 A2   5/2004

OTHER PUBLICATIONS

International Search Report and Written Opinion for PCT/AU2015/000441, dated Sep. 25, 2015 (10 pages).
(Continued)

*Primary Examiner* — Adam Baker
(74) *Attorney, Agent, or Firm* — Quarles & Brady LLP (57) ABSTRACT

An ankle brace, having a rear-entry ankle cuff adapted to be worn adjacently above lateral and medial malleoli of an ankle, and an open-heel, open-malleoli and open-toe midfoot member extending forwardly and downwardly from the ankle cuff.

12 Claims, 14 Drawing Sheets

(58) Field of Classification Search
CPC ...... A61F 13/067; A61F 13/08; A61F 13/085; A43B 7/14; A43B 7/20; A43B 7/18; A63B 71/1225; A63B 2071/1275; A61H 3/00
USPC ....... 602/11, 28, 111, 23, 27, 60, 61, 62, 63, 602/65, 66, 29
See application file for complete search history.

(56) References Cited

U.S. PATENT DOCUMENTS

| | | | | |
|---|---|---|---|---|
| 5,452,527 | A * | 9/1995 | Gaylord, Jr. | A61F 5/0195 36/110 |
| 5,527,269 | A | 6/1996 | Reithofer | |
| 5,897,520 | A * | 4/1999 | Gerig | A61F 5/0111 602/23 |
| 5,944,678 | A * | 8/1999 | Hubbard | A61F 5/0111 602/65 |
| 6,022,332 | A * | 2/2000 | Nelson | A61F 5/0111 602/65 |
| 9,393,146 | B2 * | 7/2016 | Gaylord | A61F 5/0111 |
| 9,827,131 | B2 * | 11/2017 | Watts | A61F 5/0111 |
| 2005/0222531 | A1 * | 10/2005 | Moore | A61F 5/0111 602/27 |
| 2006/0084899 | A1 * | 4/2006 | Verkade | A61F 5/0127 602/27 |
| 2007/0010773 | A1 * | 1/2007 | Watts | A61F 5/0113 602/27 |
| 2007/0021706 | A1 * | 1/2007 | Braunstein | A61F 5/0109 602/63 |
| 2008/0294082 | A1 * | 11/2008 | Chang | A61F 5/0111 602/28 |
| 2010/0036306 | A1 * | 2/2010 | Lussier | A61F 5/0111 602/65 |
| 2010/0137770 | A1 * | 6/2010 | Ingimundarson | A61F 5/0127 602/27 |
| 2011/0067271 | A1 * | 3/2011 | Foxen | A43B 3/0047 36/131 |
| 2012/0101417 | A1 * | 4/2012 | Joseph | A61F 5/01 602/5 |
| 2012/0302933 | A1 * | 11/2012 | Ostergard | A43B 5/00 602/27 |
| 2013/0138028 | A1 * | 5/2013 | Gerber | A43B 5/18 602/27 |
| 2015/0065935 | A1 * | 3/2015 | Smith | A61F 5/0111 602/27 |
| 2015/0148725 | A1 | 5/2015 | Johnsson et al. | |
| 2016/0278948 | A1 * | 9/2016 | Piercy | A43B 7/20 |

OTHER PUBLICATIONS

IPRP for International Application PCT/AU2015/000441, dated Aug. 30, 3016.
Exoform Dorsal Night Splint and Airform Night Splint [downloaded from the Internet Sep. 18, 2015] 2 pages.

* cited by examiner

FUNCTIONAL ANKLE SUPPORTS WITH IMPROVED MOVEMENT AND COMFORT

This application is a National Stage application of international application Serial No. PCT/US2018/020887, filed Mar. 5, 2018, which claims priority to U.S. provisional patent application Serial No. 62/476,280, filed Mar. 24, 2017, entitled "Learning Coach for Machine Learning System," which is incorporated herein by reference in its entirety.

FIELD

The present invention relates to functional ankle supports with improved movement and comfort.

BACKGROUND

Ankle sprains due to inward (inversion) or outward (eversion) rolling of a foot are the most frequent type of musculoskeletal injury. Many people who sprain an ankle go on to develop chronic ankle instability.

Conventional functional ankle supports have various disadvantages. Post-injury, stirrup and lace-up ankle braces restrict natural movement of the ankle joint and foot, and hence inhibit athletic performance in sports. Further, post-injury, stirrup and lace-up ankle braces are uncomfortable, and hence are typically only worn for short periods to treat ankle injuries. Conventional ankle braces therefore provide functional ankle support but compromise natural movement and comfort. As a result, conventional ankle braces are generally unsuited to being worn as everyday protective equipment to prevent ankle injuries in sports and other activities.

In this context, there is a need for ankle braces that provide functional ankle support without compromising natural movement and comfort.

SUMMARY

According to the present invention, there is provided an ankle support, comprising:
 a rear-entry ankle cuff adapted to be worn adjacently above lateral and medial malleoli of an ankle; and
 an open-heel, open-malleoli and open-toe midfoot member extending forwardly and downwardly from the ankle cuff.

The midfoot member may comprise lateral and medial members respectively extending forwardly and downwardly from the ankle cuff in front of the lateral and medial malleoli.

The lateral and medial members may further extend rearwardly below the lateral and medial malleoli towards a heel of a foot of the ankle. Rearward portions of the lateral and medial members may be releasably adjustably connected to each other by a heel strap extending around the heel.

Lower midfoot portions of one or both of the lateral and medial members may be adapted to extend around and under an arch of the foot between the heel and a fifth metatarsal bone thereof to be adjustably releasably connectable to each other. The lower midfoot portions of the lateral and medial members may be adjustably releasably connectable to each other either under the foot or on a medial side thereof, and either interiorly or exteriorly of a shoe. When the lower midfoot portions of the lateral and medial members are adjustably releasably connectable to each other exteriorly of the shoe, the ankle support may be a spat for the shoe.

The lateral and medial members may be adjustably releasably connectable to each other by hook-and-loop fastener strips moulded to respective overlapping ends of the lower midfoot portions.

A slot may be provided through the lower midfoot portion of one of the lateral and medial members, and a pull tab may be provided on the lower midfoot portion of the other of the lateral and medial members, wherein pulling the pull tab through the slot adjustably tensions the medial and lateral members against each other.

The ankle cuff and the midfoot member may have a unitary one-piece construction. The ankle cuff and the midfoot member may be integrally moulded together in an elastically deformable polymeric material. The elastically deformable polymeric material may be thermoplastic urethane (TPU).

The ankle support may further comprise padding bonded to interior surfaces of the ankle cuff, and to upper interior surfaces of the lateral and medial members. The padding may comprise EVA (ethylene vinyl acetate copolymer) foam.

The ankle support may further comprise a free-floating liner extending downwardly from the padding to overlie lower interior surfaces of the lateral and medial members. The liner may comprise neoprene.

BRIEF DESCRIPTION OF DRAWINGS

Embodiments of the invention will now be described by way of example only with reference to the accompanying drawing, in which.

DESCRIPTION OF EMBODIMENTS

Referring to the drawings, an ankle support 10 according to an embodiment of the present invention generally comprises a rear-entry ankle cuff 12 adapted to be worn adjacently above, or partially overlapping above, lateral and medial malleoli of an ankle, and an open-heel, open-malleoli and open-toe midfoot member 14 extending forwardly and downwardly from the ankle cuff 12. The midfoot member 14 may comprise lateral and medial members 16, 18 respectively extending forwardly and downwardly from the ankle cuff 12 in front of the lateral and medial malleoli. At least a portion of the midfoot member 14 may be adapted to be worn adjacent to an upper midfoot portion of, or around, a foot of a wearer. Ridges 19 may be provided on a forward upper portion 21 of the midfoot portion 14 to grip an underside of a tongue of shoe.

The lateral and medial members 16, 18 may further extend rearwardly below the lateral and medial malleoli towards a heel of a foot of the ankle. Holes 17 may be provided through rearward portions of the lateral and medial members 16, 18 for ventilation, or for use as mounting holes for post-and-hole connections of optional modular components such as heel caps or C-springs (not shown). Lower midfoot portions 20, 22 of one or both of the lateral and medial members 16, 18 may be adapted to extend around and under an arch of the foot between the heel and a fifth metatarsal bone thereof to be adjustably releasably connectable to each other. A lower front edge portion 23 of lower midfoot portion 20 of the medial member 18 may be adapted to abut and/or anchor adjacent to the fifth metatarsal bone. The lower midfoot portions 20, 22 of the lateral and medial members 16, 18 may be adjustably releasably connectable to under the foot interiorly of a shoe and over a sock.

Figure 1:
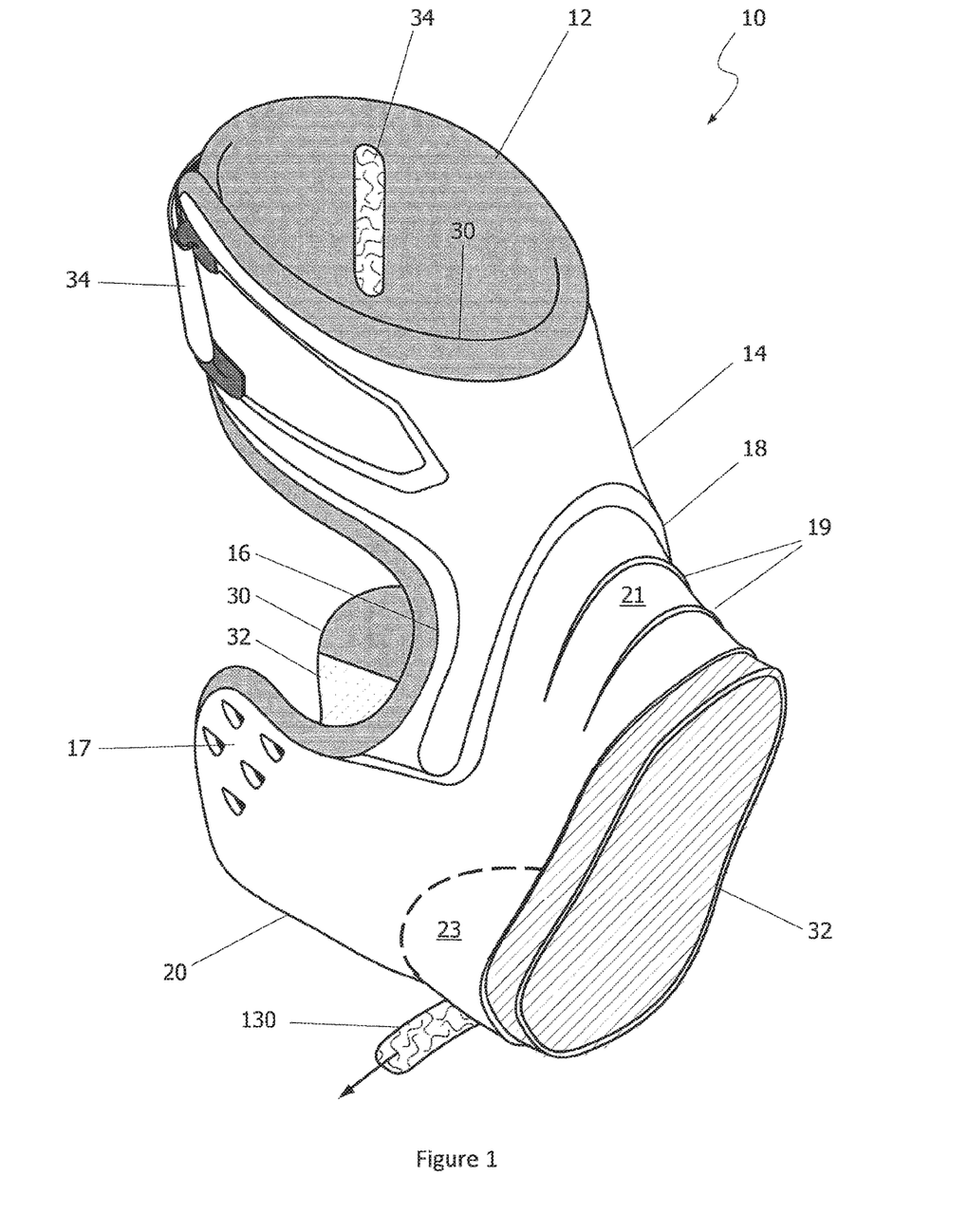
FIGS. 1 and 2 are front and exploded perspective views of an ankle support according an embodiment of the present invention.
Figure 2:
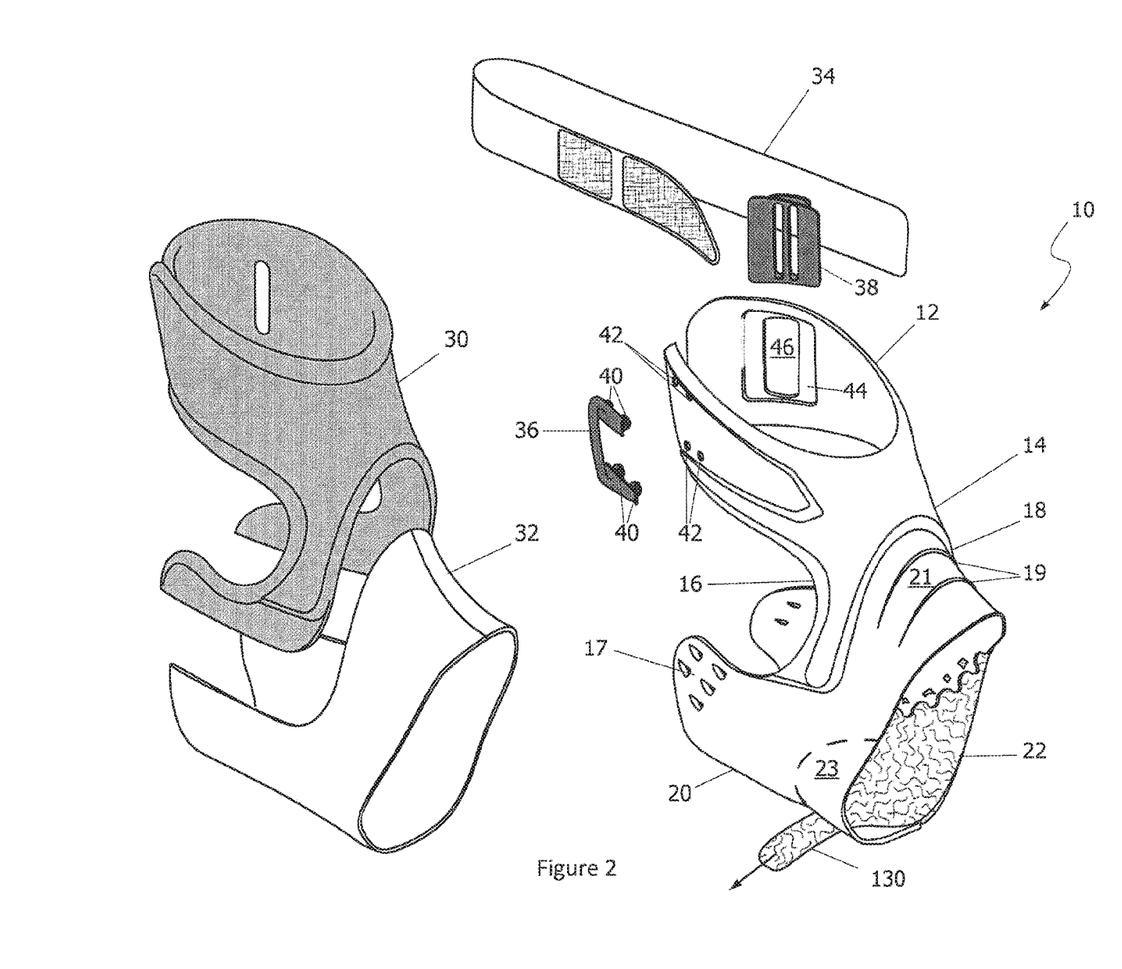
Figure 3:
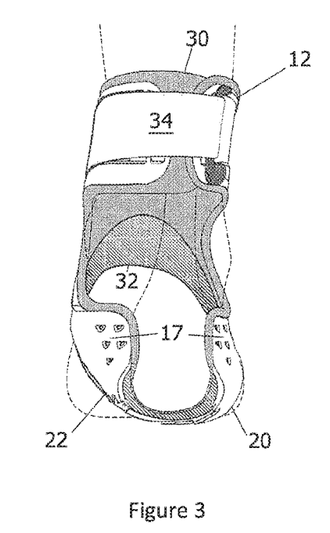
FIGS. 3 to 8 are end, side, bottom and plan views of the ankle support.
Figure 4:
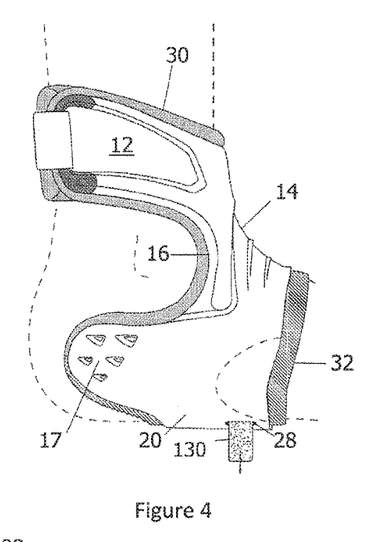
Figure 5:
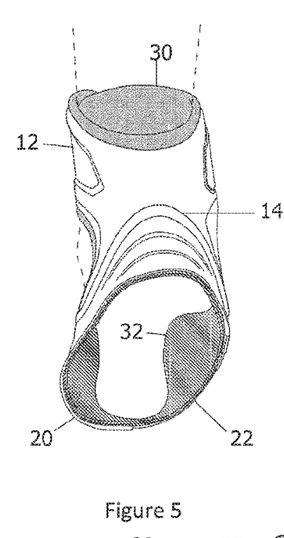
Figure 6:
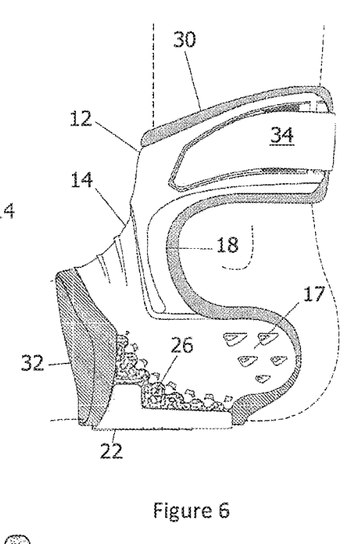
Figure 7:
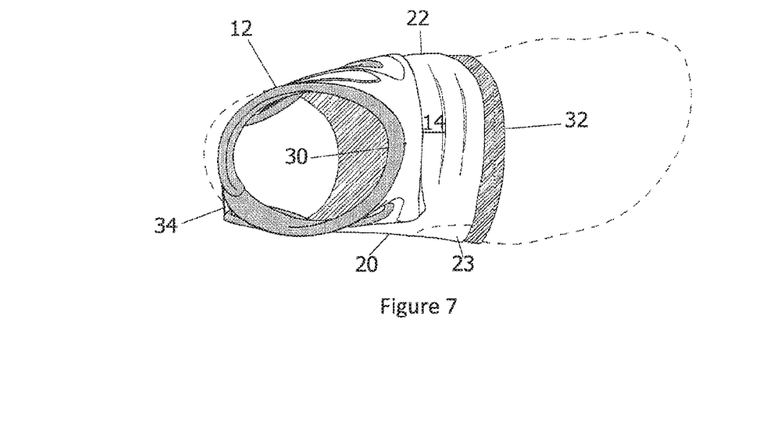
Figure 8:
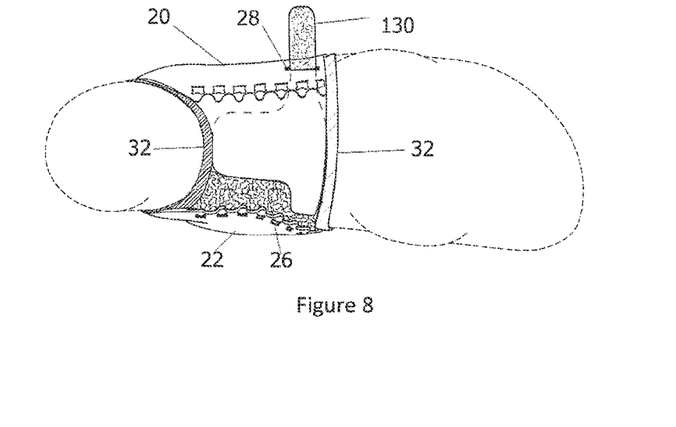
Figure 9:
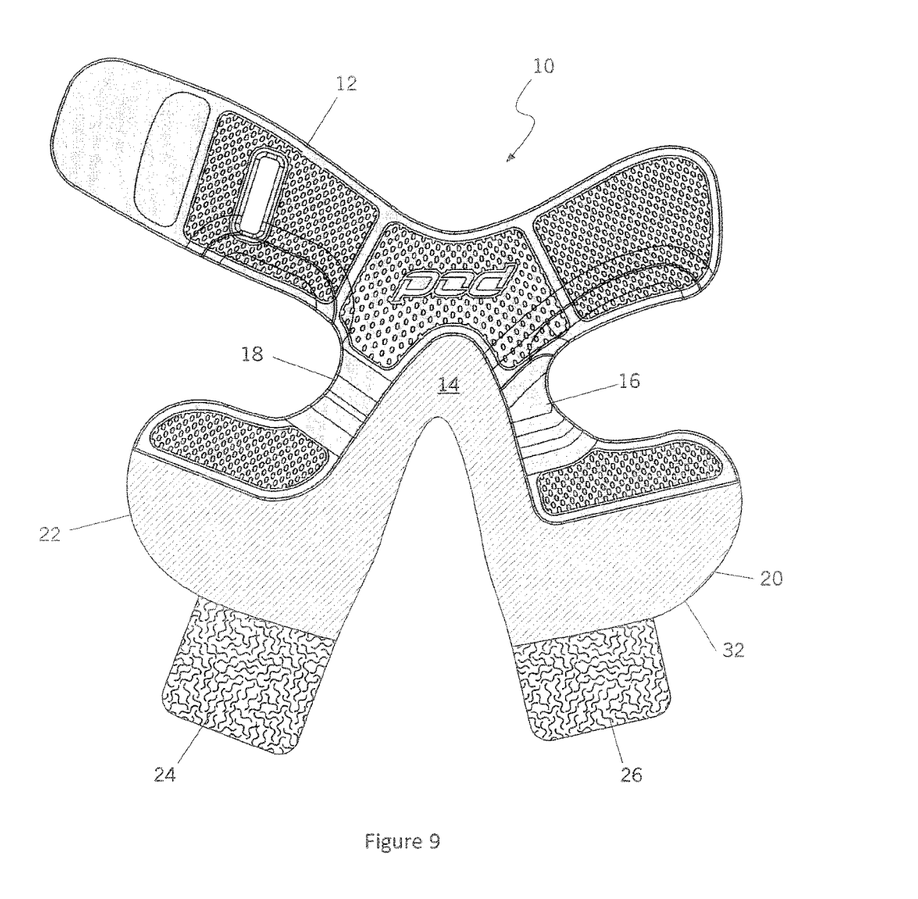
FIG. 9 is a plan view of the interior of the ankle support in a laid flat state.
Figure 10:
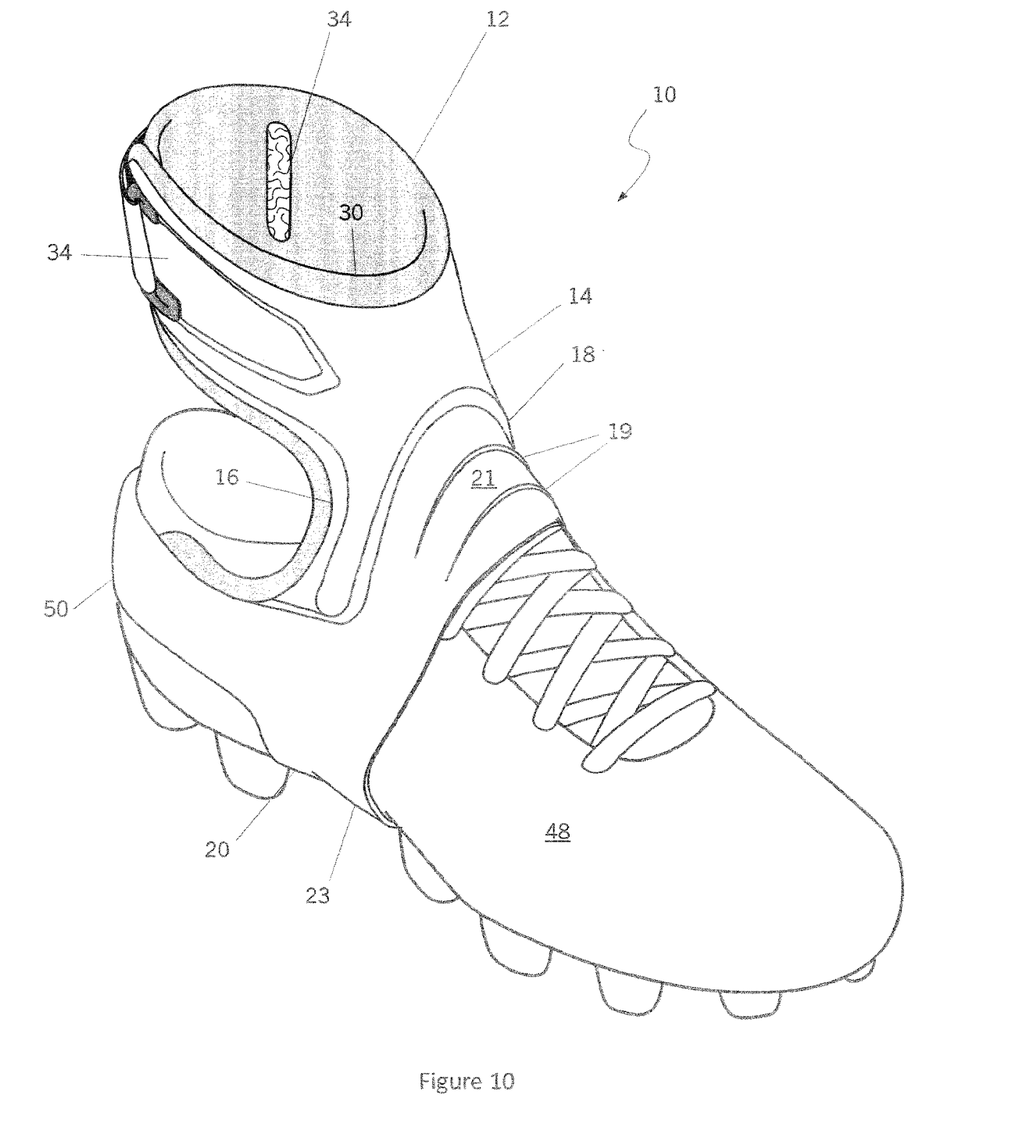
FIGS. 10 and 11 are front and exploded perspective views of the ankle support implemented as a spat for a shoe.
Figure 11:
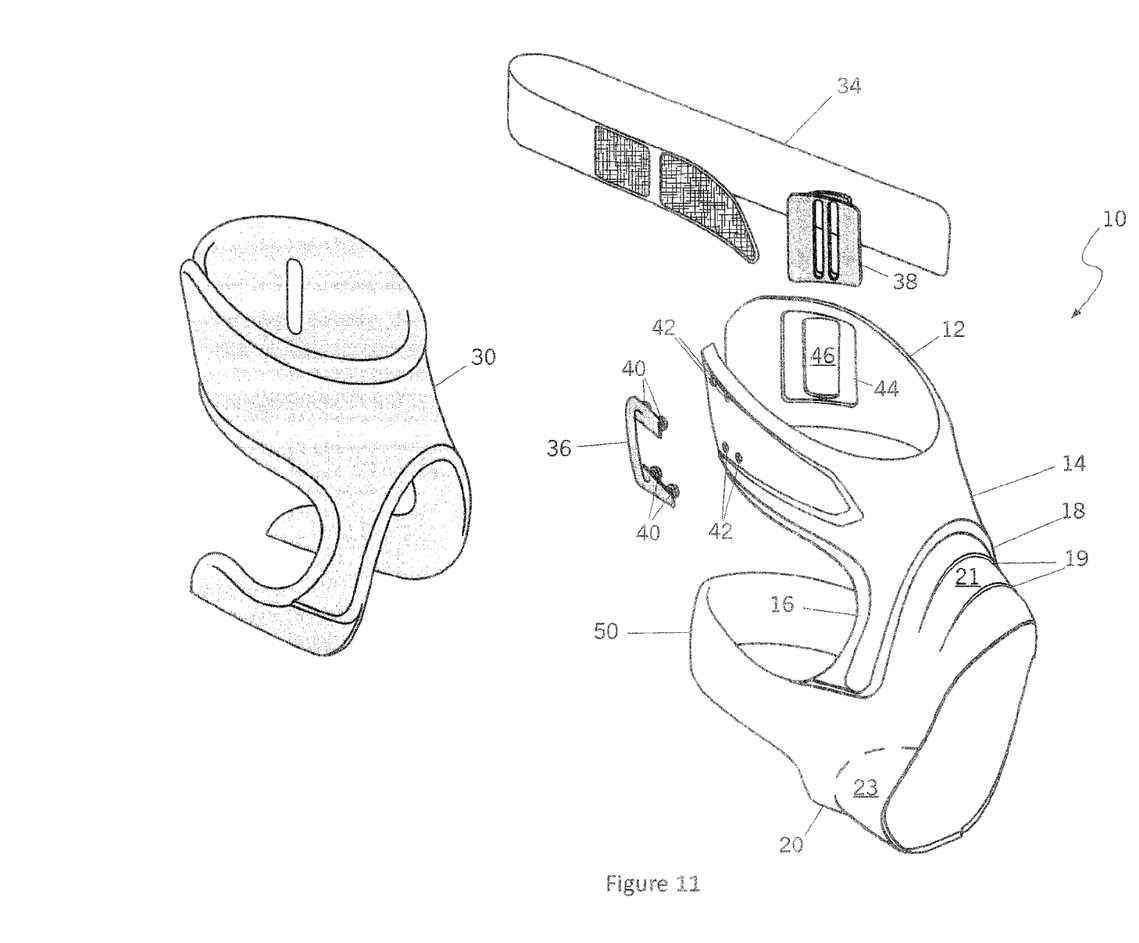
Figure 12:
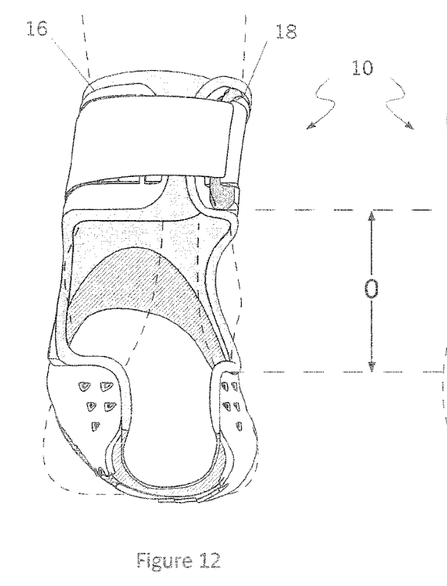
FIGS. 12 to 19 are end, side and front view of the ankle support in different positions during use.
Figure 13:
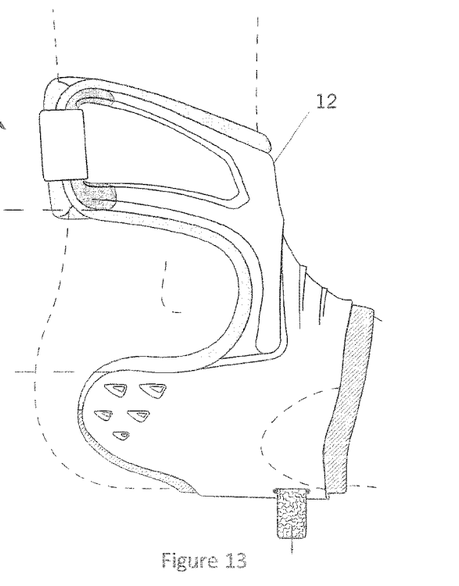
Figure 14:
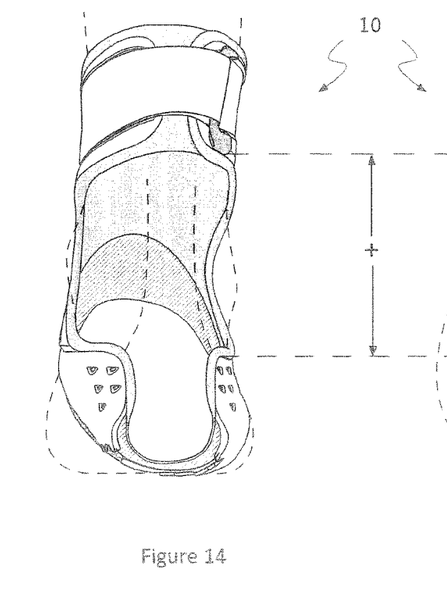
Figure 15:
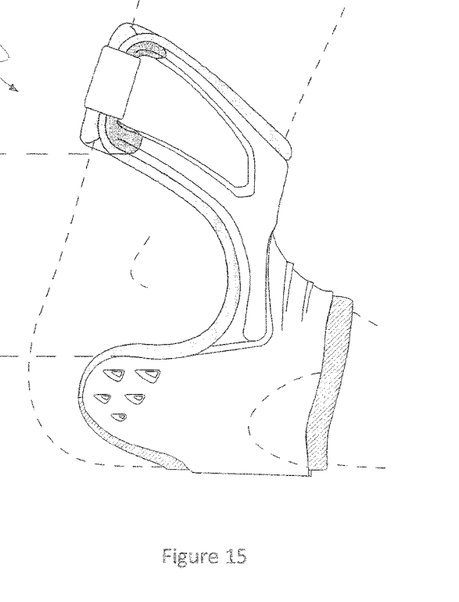
Figures 16, 17:
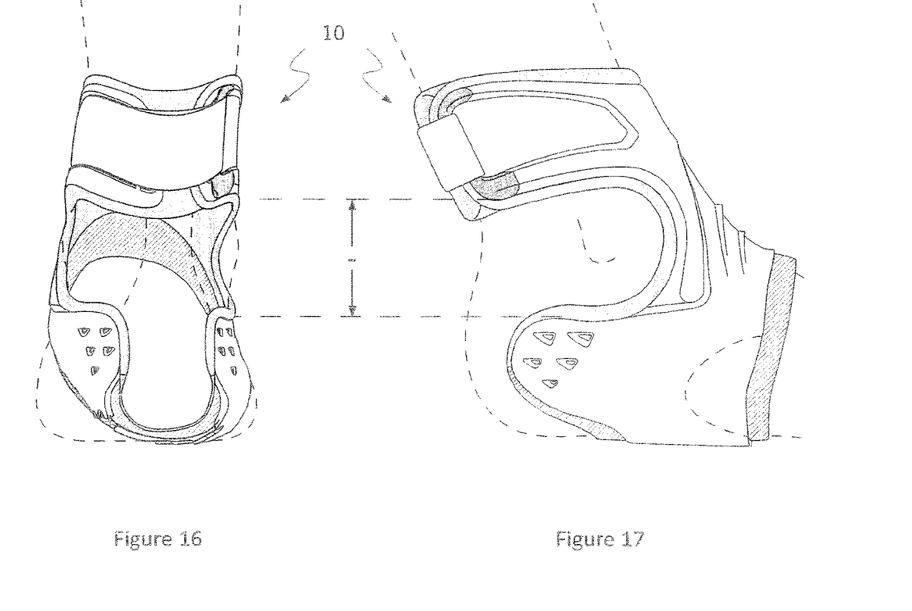
Figures 18, 19:
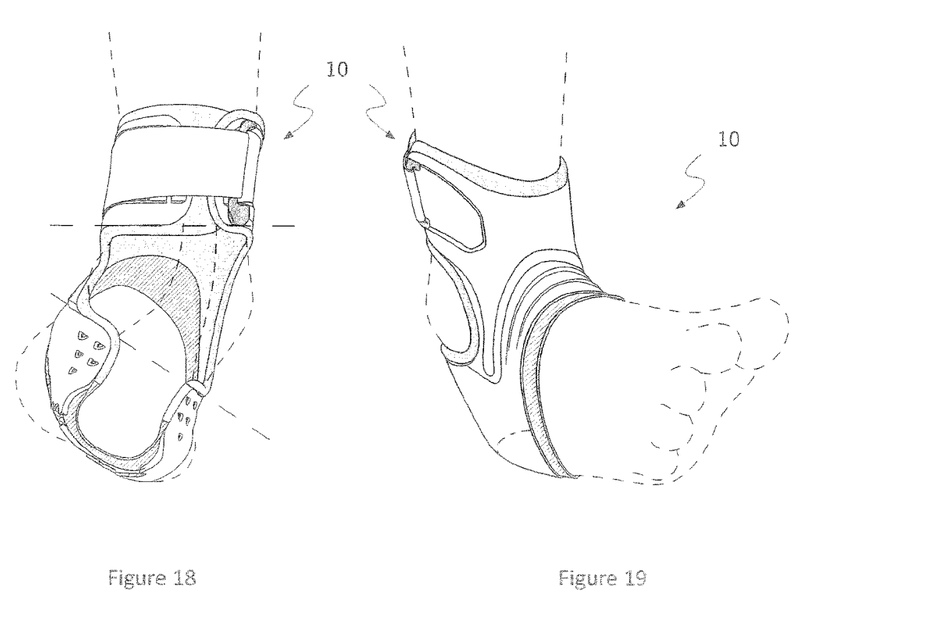

Referring to FIG. 9, the lateral and medial members may be adjustably releasably connectable to each other by complementary low-profile hook-and-loop fastener strips 24, 26 moulded to respective overlapping ends of the lower midfoot portions 20, 22 of the lateral and medial members 16, 18. The lower midfoot portions 20, 22 of the lateral and medial members 16, 18 may adjustably releasably connect to each other under the foot in various overlapping relationships to flexibly accommodate different foot sizes, shapes, widths and arch heights. As best seen in FIGS. 4 and 8, a slot 28 may be provided through the lower midfoot portion 20 of the lateral member 16, and a pull tab 30 may be provided on the lower midfoot portion of the medial member 18 so that in use pulling the pull tab 30 through the slot 28 adjustably tensions the medial member 18 against the lateral member 16. It will be appreciated that the arrangement of the slot and pull tab on the lateral and medial members 16, 18 may be reversed. The tensioning mechanism provided by the slot 28 and pull tab 30 may allow the midfoot member 14 to be securely anchored to and comfortably fitted under the arch of the midfoot of a wearer. The pull tab 30 may be permanent, or optionally sacrificial to be cut or broken off the medial member 18 after initial tensioning.

The ankle cuff 12 and the midfoot member 14 may have a unitary one-piece construction. For example, the ankle cuff 12 and the midfoot member 14 may be integrally moulded together in an elastically deformable polymeric material. The elastically deformable polymeric material may, for example, be thermoplastic urethane (TPU) such as Skythane™ or Estane™. Other equivalent or alternative elastically deformable polymeric materials having a high elastic modulus may also be used.

Figure 26:
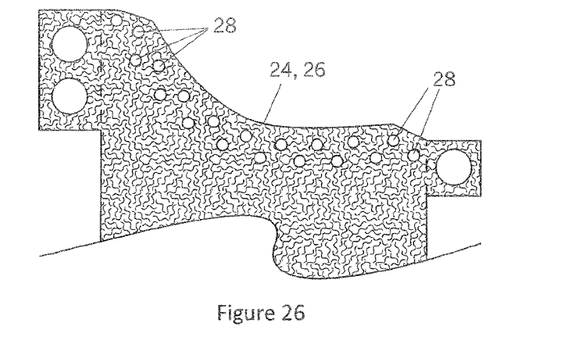
FIGS. 26 to 28 are detailed plan views of moulding over and through hook-and-loop fasteners of the ankle support.
Figure 27:
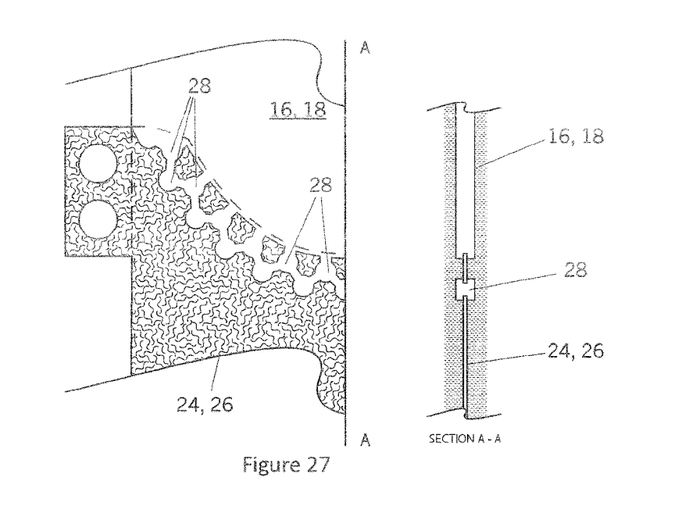
Figure 28:
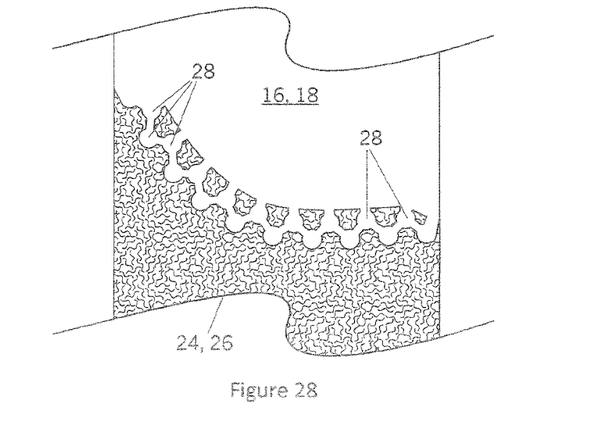

Referring to FIGS. 26 to 28, the low-profile hook-and-loop fastener strips 24, 26 may be moulded to respective ends of the lower midfoot portions 20, 22 by die cutting spaced-apart through holes 28 adjacent to respective edges of the hook-and-loop fastener strips 24, 26. The elastically deformable polymeric material moulded to form the lower midfoot portions 20, 22 may be simultaneously injection moulded through the spaced-apart through holes 28 to form a lattice (or interlaced structure or pattern) of interconnected through- and over-mouldings that securely anchor the hook-and-loop fastener strips 24, 26 to the respective ends of the lower midfoot portions 20, 22. Other equivalent or alternative methods of moulding over and through the hook-and-loop fastener strips 24, 26 to mould them to the respective ends of the lower midfoot portions 20, 22 may also be used.

The ankle support 10 may further comprise padding 30 bonded to interior surfaces of the ankle cuff 12, and to upper interior surfaces of the lateral and medial members 16, 18. The padding 30 may, for example, comprise EVA (ethylene vinyl acetate copolymer) foam. Other equivalent or alternative padding materials may also be used. The ankle support 10 may further comprise a free-floating underfoot liner 32 extending downwardly from the padding 30 to overlie lower interior surfaces of the lateral and medial members 16, 18. The liner 32 may be bonded and/or sewn to the padding 30. The liner 32 may, for example, comprise neoprene. Other equivalent or alternative liner materials may also be used.

The ankle support 10 may further comprise an adjustment strap 34 removably threadably connected to the ankle cuff 12 by lateral and medial anchor posts 36, 38. The lateral and medial anchor posts 36, 38 may be respectively mounted to lateral and medial portions of the ankle cuff 12 by press fitting. For example, the lateral anchor post 36 may comprise headed posts 40 that press fit into through holes 42 provided in the lateral portion of the ankle cuff 12. The medial anchor post 38 may press fit into internal recess 44 and through a cut-out 46 provided in the medial portion of the ankle cuff 12. The lateral and medial anchor posts 36, 38 may be mouldings in a polymeric material that is relatively more rigid than the TPU of the ankle cuff 12. For example, the lateral and medial anchor posts 36, 38 may be mouldings in nylon or polypropylene.

Figure 20:
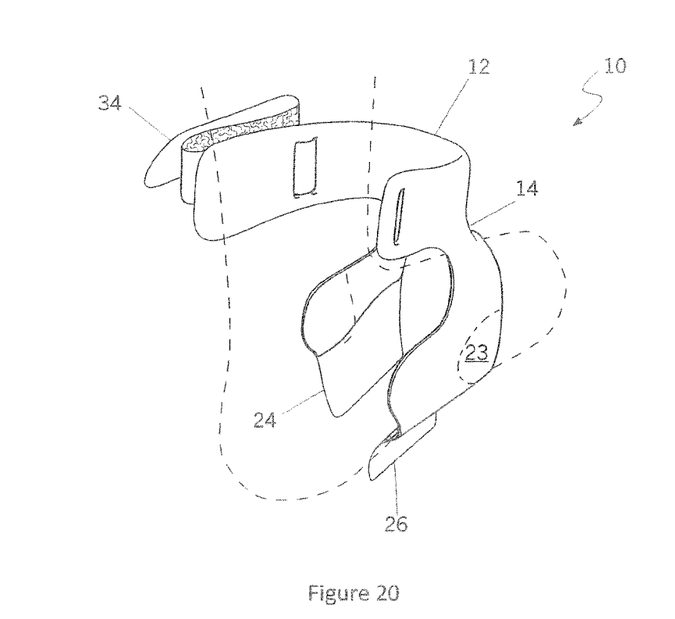
FIGS. 20 to 23 are rear perspective, top section, bottom and side views showing fitment of the ankle support to a wearer's ankle and foot.
Figure 21:
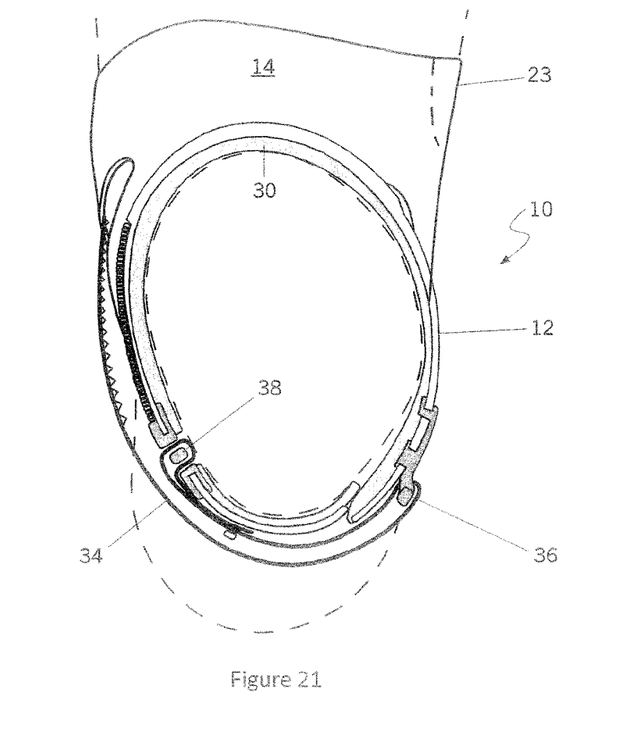
Figure 22:
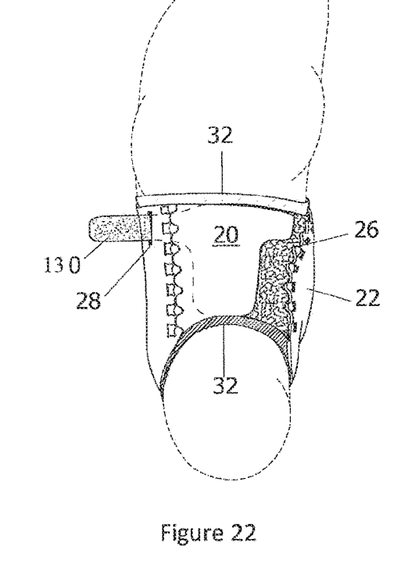
Figure 23:
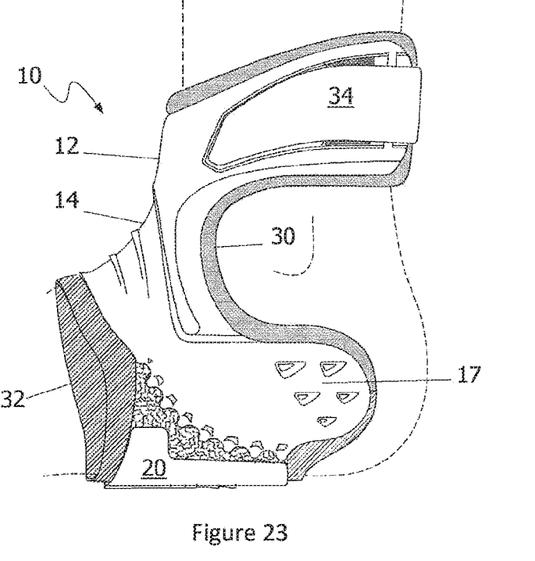
Figure 24:
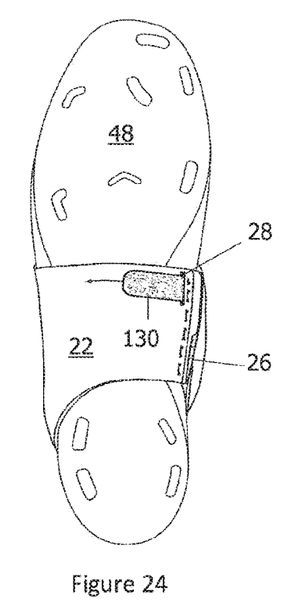
FIGS. 24 and 25 are bottom and side views of the spat embodiment of the ankle support.

FIGS. 20 and 21 illustrate adjustment of the adjustment strap 34 of the ankle cuff 12. The adjustment strap 34 may be threaded through and tensioned against the lateral and medial anchor posts 36, 38, and then looped back to overlie exterior of the medial portion of the ankle cuff 12. One end of the adjustment strap 34 may have spaced-apart complementary low-profile hook-and-loop fastener strips that engage to anchor around the medial anchor post 36. Complementary low-profile hook-and-loop fastener strips may also be respectively provided on the other free end of the cuff adjustment strap 34 and the exterior of the medial portion of the ankle cuff 12.

FIGS. 12 to 19 illustrate that, in use, the ankle support 10 may provide functional ankle support to prevent and/or treat ankle injury, while also providing significantly increased degrees of natural ankle movement in plantar flexion and dorsiflexion, and inversion and eversion. While it is not intended to be bound to any particular theory, it is believed that the ankle cuff 12 and medial and lateral members 16, 18 of the midfoot member 14 generate passive opposing/resistive torques to support and protect the major ligaments in the ankle joint. For example, the anterior talofibular ligament (ATFL) originates from the lateral malleolus of the Fibula and inserts into the lateral surface of the talus. Further, the calcaneofibular ligament (CFL) originates from the lateral malleolus of the fibula and inserts into the lateral surface of the calcaneous. In the case of pure inversion, the ankle support 10 may experience a tensile force that results in an opposing torque acting about a rotational axis similar to that acting as a result of the CFL under load. In the case of combined plantar flexion and inversion, the ankle support 10 may experience a tensile force that results in an opposing torque acting about a rotational axis similar to that acting as a result of the ATFL under load.

Further, it is believed that the ankle support 10 may offer an alternate load path to indirectly replicate the action of the ATFL and to a lesser extent, the CFL. It may provide this by restricting the extent to which the whole foot can rotate relative to the lower leg. As the ankle inverts, the urethane shell across the lateral anterior area of the ankle support 10 experiences tensile stress. This tensile stress may cause the ankle cuff 12 to pull down and anchor above the malleoli. Meanwhile the in-shoe portion of the ankle support 10 may capture the fifth metatarsal region of the foot, causing a resistive torque that acts to oppose the external force causing the injurious ankle inversion. This opposing torque may work to reduce the inversion rate of the ankle joint as a whole, which in turn results in a reduced inversion angle. The reduction in inversion rate and angle translates to a reduced degree of rotation of the bones in the ankle joint, particularly the talus and calcaneous. This may result in a reduced magnitude of strain experienced by the ligaments that connect these bones to the fibular and tibia bones of the lower leg. This may in turn reduce the likelihood of injury to these ligaments. The higher the degree of plantar flexion (pointing toes down) during inversion, the higher the tensile stress experienced by the ankle support 10 and the higher the opposing torque.

Further to the fifth metatarsal capture by the ankle support 10 described above, the padding and liner across the anterior and lateral surface of the foot may compress against the skin under load to serve two purposes. First, this compression may prevent slippage between the ankle support 10 and foot by enhancing the capacity to transfer shear forces between the ankle support 10 and the wearer's skin. This may also have a net effect of increasing the torque opposing the external inversion forces. Second, the compression may create a light pressure force across a large surface of the ankle joint such that the wearer may feel the ankle support 10 resisting inversion. The higher the inversion angle, the higher the pressure. This in turn may assist the wearer's proprioceptive capacity by providing enhanced feedback for the wearer to know the orientation of their ankle. This may in turn allow the wearer to better coordinate the movement of their ankle through greater ankle muscle coordination and thereby reduce the likelihood of ankle injury. Other equivalent or alternative biomechanical modes of action to reduce and/or treat ankle injury may also be provided by the ankle support 10.

Figure 25:
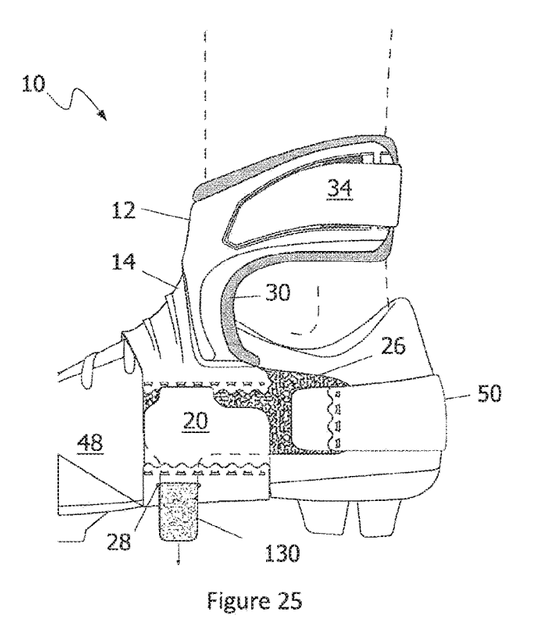

FIGS. 10, 11, 24 and 25 illustrate another embodiment of the ankle support 10 that may be implemented as a spat for a cleated sports shoe. This over-shoe spat embodiment of the ankle support 10 may have the same general components and configuration as the previous in-shoe embodiment described above. The exceptions are that the lower midfoot portions of the lateral and medial members 16, 18 may be adjustably releasably connectable to each other either on a medial side of the foot exteriorly of a shoe 48. Further, rearward portions of the lateral and medial members may be releasably adjustably connected to each other by a heel strap 50 extending around the heel. Further, the free-floating underfoot liner 32 is omitted. As best seen in FIG. 25, the lower midfoot portion of the lateral member 16 may extend down, under and around an underfoot portion of the shoe 48 forwardly of the rear cleats to overlap the lower midfoot portion of the medial member 18. The overlapping ends of the lateral and medial members 16, 18 may be releasably adjustably connected to each other on the medial side of the shoe by complementary low-profile hook-and-loop fastener strips. Further, the heel strap 50 may also be releasably adjustably connected to the lateral and medial members 16, 18 on the medial side of the shoe by complementary low-profile hook-and-loop fastener strips. In this embodiment, the slot and pull tab tensioning mechanism 28, 30 may be provided on the medial side of the ankle support 10. Lower portions of one or both of the lateral and medial members overlying the shoe may be wholly or partially transparent so as to allow branding or indicia on the shoe 50 to be externally visible therethrough.

Figure 29:
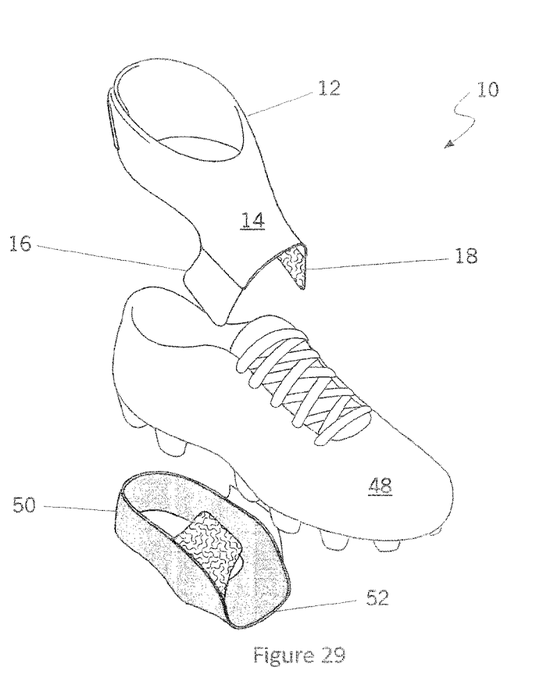
FIG. 29 is an exploded perspective view of an alternative spat embodiment of the ankle support.

FIG. 29 illustrates an alternative spat embodiment of the ankle support 10 in which the lateral and medial members 16, 18 of the midfoot member 14 may be releasably adjustably connectable to a separate underfoot section 52 by complementary low-profile hook-and-loop fasteners on lateral and medial sides of the shoe. The underfoot section 52 may comprise lateral and medial side portions interconnected by a heel strap 50. A cut-out may be provided in the underfoot section 52 to surround the rear cleats of the shoe 48. Other equivalent or alternative spat embodiments of the ankle support 10 may also be used.

Figure 30:
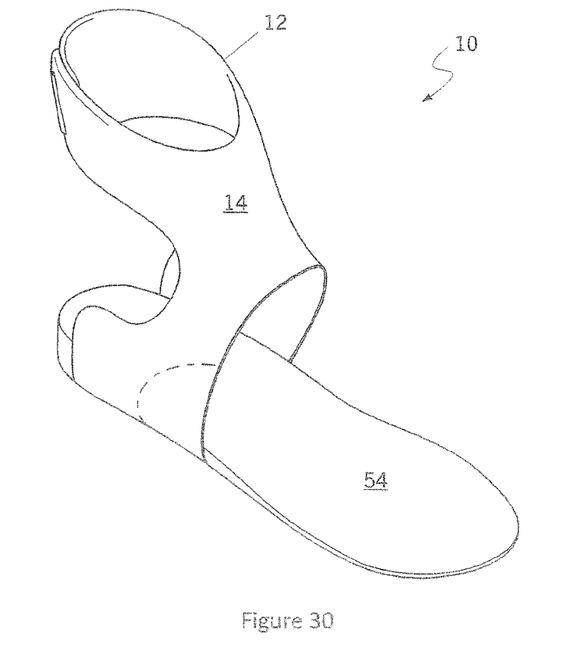
FIGS. 30 to 33 are perspective views of embodiments of the ankle support implemented as parts of footwear.
Figure 31:
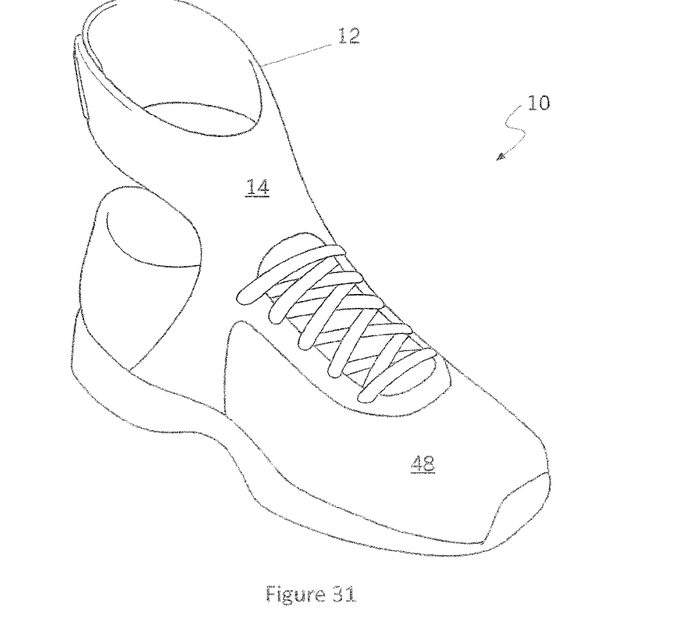

FIGS. 30 to 34 illustrate that other embodiments of the ankle support 10 may be integrated with, or directly or indirectly connected to, sports, work and everyday footwear, such as shoes and boots. For example, FIG. 30 illustrates an embodiment of the ankle support 10 in which the midfoot member 14 is connected to or incorporates an orthotic shoe insert, insole or footbed 54. In other footwear embodiments, the midfoot member 14 of the ankle support 10 may be directly or indirectly connected to lateral and medial sides of an upper of a shoe 48, as illustrated in FIG. 31. When the shoe upper has a knitted or woven fabric construction, the ankle support 10 may also have a knitted or woven fabric construction that is either integrally knitted or woven into the shoe upper. Further or alternatively, the ankle support 10 may be attached onto the shoe upper through stitching, gluing, fusing or bonding to become an integral part of the final shoe upper.

Figure 32:
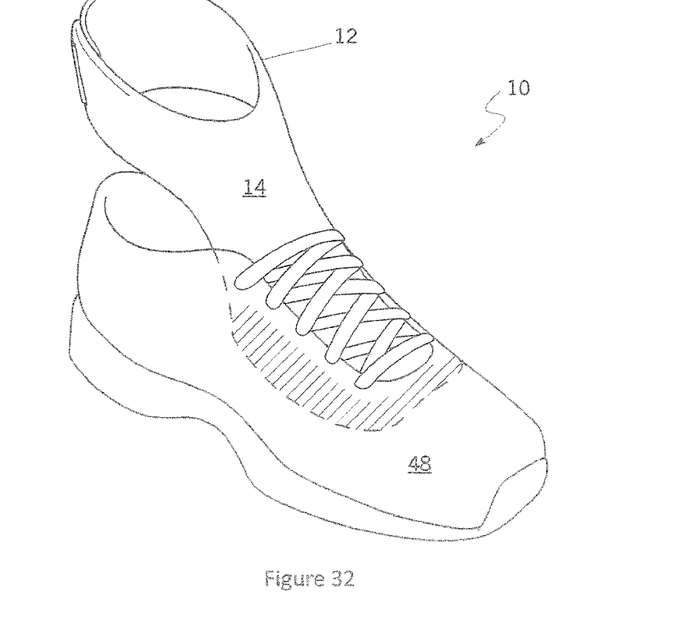
Figure 33:
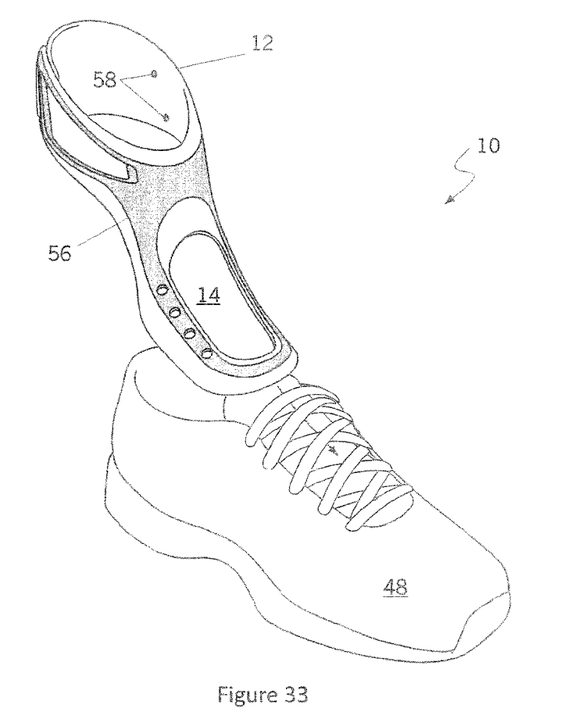

FIG. 32 illustrates that the midfoot member 14 of the ankle support 10 may integrally form, or be directly or indirectly connected to, a tongue of a shoe 48. For example, FIG. 33 illustrates that the ankle support 10 may be embodied as a standalone shoe tongue insert that may be inserted either between a shoe tongue and footwear laces 28, or under the shoe tongue. In this embodiment, the ankle cuff 12 and the midfoot portion 14 may be reinforced by a resilient exoskeleton 56. The resilient exoskeleton 56 may be removably connected to the ankle cuff 12 and the midfoot portion 14 by post-and-hole connections 58. For example, posts may be provided on the resilient exoskeleton 56 that press fit into holes provided through the ankle cuff 12. The resilient exoskeleton may be a moulding in a polymeric material that is relatively more rigid than the TPU of the ankle cuff 12 and the midfoot member 14, for example, nylon or polypropylene.

Figure 34:
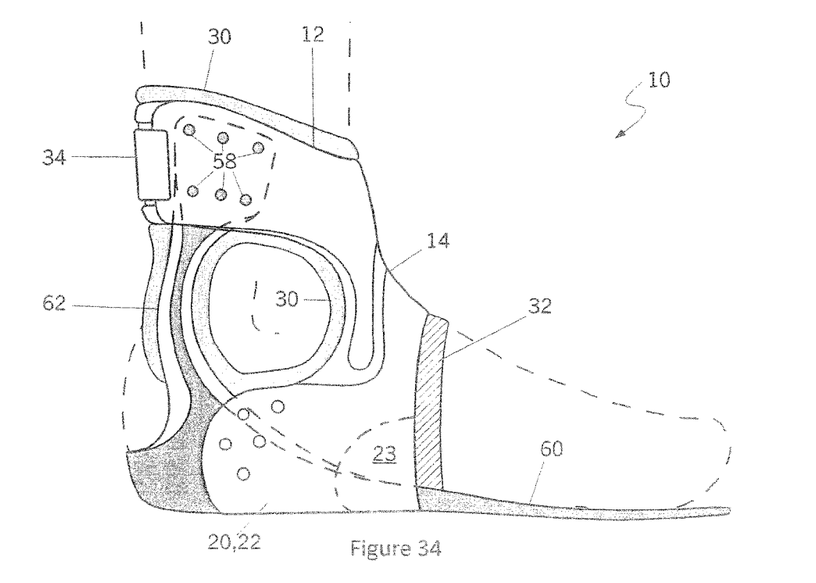
FIG. 34 is a side view of an embodiment of the ankle support implemented with a foot base and C-springs.

FIG. 34 illustrates a further embodiment of the ankle support 10 that incorporates a rigid or semi-rigid foot base 60 resiliently suspended from the ankle cuff 12 by a pair of forwardly curved resilient C-springs 62. The C-springs 62 may be removably connected to the ankle cuff 12 by post-and-hole connections 58. For example, posts may be provided on the C-springs 62 that press fit into holes provided through the ankle cuff 12. The use of C-springs 62 is described in further detail in the present applicant's WO 2013/188915 which is hereby incorporated in its entirety.

Embodiments of the present invention provide functional ankle supports with improved natural movement and comfort that are useful for everyday use to prevent and/or treat ankle injuries.

For the purpose of this specification, the word "comprising" means "including but not limited to", and the word "comprises" has a corresponding meaning.

The embodiments have been described by way of example only and modifications are possible within the scope of the claims that follow.

The invention claimed is:

1. A functional ankle brace to prevent or treat ankle injury, the ankle brace comprising:
   a rear-entry ankle cuff adapted to be worn adjacently above lateral and medial malleoli of an ankle, such that the ankle cuff when worn by a user is closer to the ankle than to a knee of the user; and
   an open-heel, open-malleoli and open-toe midfoot member extending forwardly and downwardly from the ankle cuff;
   wherein the ankle cuff and the midfoot member have a unitary one-piece construction of an elastically deformable polymeric material;
   wherein the ankle cuff extends rearwardly above the lateral and medial malleoli;
   wherein the midfoot member extends rearwardly below the lateral and medial malleoli;
   wherein the ankle cuff and the midfoot member neither extend completely around nor over the lateral and medial malleoli so that in use the lateral and medial malleoli are neither completely surrounded nor covered;
   wherein the midfoot member comprises lower midfoot portions that are adapted to extend under an arch of the user, wherein the lower midfoot portions are adjustable releasably connectable to each other; and
   wherein the midfoot member includes a first portion located below the lateral malleolus and a second portion located below the medial malleolus, each of the first and second portions including an upper boundary extending rearwardly away from the respective malleolus to a rearwardmost location between the malleolus and a back of the user's foot and a lower boundary extending from the rearwardmost location toward the lower midfoot portions of the midfoot member.

2. The functional ankle brace of claim 1, wherein the ankle cuff and the midfoot member are integrally moulded together in an elastically deformable polymeric material.

3. The functional ankle brace of claim 2, wherein the elastically deformable polymeric material is thermoplastic polyurethane (TPU).

4. The functional ankle brace of claim 1, further comprising padding bonded to interior surfaces of the ankle cuff, and to upper interior surfaces of the midfoot member.

5. The functional ankle brace of claim 4, wherein the padding comprises EVA (ethylene vinyl acetate copolymer) foam.

6. The functional ankle brace of claim 4, further comprising a free-floating liner extending downwardly from the padding to overlie lower interior surfaces of the midfoot member.

7. The functional ankle brace of claim 1, wherein the midfoot member first and second portions are releasably adjustably connected to each other by a heel strap extending around the heel.

8. The functional ankle brace of claim 1, wherein the midfoot member lower midfoot portions are adapted to extend under the arch of the foot between the heel and a fifth metatarsal bone thereof to be adjustably releasably connectable to each other.

9. The functional ankle brace of claim 8, wherein lower midfoot portions are adjustably releasably connectable to each other either, such that the lower midfoot portions are connectable around both the user's foot inside a shoe of the user and exteriorly around the shoe of the user.

10. The functional ankle brace of claim 1, wherein the midfoot member comprises lateral and medial members that are connectable to each other by hook-and loop fastener strips moulded respectively thereto.

11. The functional ankle brace of claim 1, wherein the midfoot member is integrally formed, or is connected to, a tongue of a shoe.

12. The functional ankle brace of claim 1, wherein the ankle brace allows for of natural movement in plantar flexion and dorsiflexion, and inversion and eversion.

* * * * *